United States Patent
Falsetti et al.

(10) Patent No.: US 7,017,414 B2
(45) Date of Patent: Mar. 28, 2006

(54) ULTRASONIC INSPECTION METHOD AND SYSTEM THEREFOR

(75) Inventors: Robert V. Falsetti, Schenectady, NY (US); Curtis Wayne Rose, Mechanicville, NY (US)

(73) Assignee: General Electric Company, Schenectady, NY (US)

( * ) Notice: Subject to any disclaimer, the term of this patent is extended or adjusted under 35 U.S.C. 154(b) by 119 days.

(21) Appl. No.: 10/604,559

(22) Filed: Jul. 30, 2003

(65) Prior Publication Data

US 2005/0022602 A1    Feb. 3, 2005

(51) Int. Cl.
*G01N 29/04* (2006.01)
(52) U.S. Cl. .................. 73/600; 73/602; 73/622; 73/628; 73/641
(58) Field of Classification Search ............. 73/597, 73/598, 599, 600, 618, 625, 628, 660, 619, 73/620, 622, 602, 641
See application file for complete search history.

(56) References Cited

U.S. PATENT DOCUMENTS

| | | | | |
|---|---|---|---|---|
| 3,597,963 A | * | 8/1971 | Smejkal et al. | ......... 73/660 |
| 4,441,369 A | | 4/1984 | Lessard et al. | ......... 73/602 |
| 4,660,419 A | * | 4/1987 | Derkacs et al. | ......... 73/622 |
| 4,864,862 A | * | 9/1989 | Nottingham et al. | ......... 73/623 |
| 5,189,915 A | | 3/1993 | Reinhart et al. | ......... 73/623 |
| 5,618,994 A | | 4/1997 | Falsetti | ......... 73/602 |
| 6,065,344 A | * | 5/2000 | Nolan et al. | ......... 73/629 |
| 6,082,198 A | | 7/2000 | Sabourin et al. | ......... 73/633 |
| 6,370,956 B1 | | 4/2002 | Bewlay et al. | ......... 73/599 |
| 6,401,537 B1 | | 6/2002 | Gigliotti et al. | ......... 73/598 |
| 6,487,909 B1 | | 12/2002 | Harrold et al. | ......... 73/593 |
| 6,725,722 B1 | * | 4/2004 | Murphy et al. | ......... 73/628 |

* cited by examiner

*Primary Examiner*—Hezron Williams
*Assistant Examiner*—Nashmiya Fayyaz
(74) *Attorney, Agent, or Firm*—Ernest Cusick; Gary M. Hartman; Domenica N. S. Hartman

(57) ABSTRACT

A method and system for ultrasonically inspecting turbine wheels and other disk-shaped articles having a central opening and multiple secondary openings radially spaced outward from the central opening. At least one ultrasonic transducer is placed in at least one of the secondary openings of the wheel. The transducer is configured and oriented to perform a pulse-echo diagnostic technique on the wheel by emitting ultrasonic signals that intersect radials of the wheel at angles of approximately ninety degrees to the radials. The ultrasonic signals intersect the radials at points so that a plurality of points are located on a plurality of radials. The points define a locus of points through the volume of the wheel between the central opening and the secondary opening, such that the volume is inspected for defects. The transducer receives ultrasonic signals that are reflected from one or more points when a defect is encountered.

19 Claims, 2 Drawing Sheets

ULTRASONIC INSPECTION METHOD AND SYSTEM THEREFOR

BACKGROUND OF INVENTION

1. Field of the Invention

The present invention generally relates to ultrasonic inspection methods and systems. More particularly, this invention relates to a method and system for ultrasonically inspecting a disk-shaped article having a central opening and a plurality of circumferentially-spaced secondary openings that are radially spaced outward from the central opening, such as a turbine wheel or disk, wherein ultrasonic signals are generated and received by transducers placed in the secondary openings.

2. Description of the Related Art

Ultrasonic inspection techniques have been widely used to perform nondestructive testing on articles formed of materials having an intrinsically coarse grain structure, which results in anisotropic and nonuniform acoustic properties. Particular examples of such articles include forged super-alloy turbine wheels (rotors) used in gas and steam turbines. In the hostile operating environments of gas and steam turbines, the structural integrity of the turbine wheel is of great importance in view of the high mechanical stresses that wheels must be able to continuously withstand at extremely high temperatures.

Ultrasonic inspection techniques employed with turbine wheels have typically involved inspecting each forging from a plane perpendicular to the highest operating stresses, i.e., ultrasonic transducers are placed on the fore and/or aft surfaces transverse to the rotational axis of a turbine wheel. With this approach, the ultrasonic energy is generated in a direction substantially perpendicular to the orientation of the most common defects, which tend to lie in axial-radial planes of a turbine wheel. Two ultrasonic testing techniques have been conventionally used, a first of which is a pitch-catch technique using two transducers placed on the fore and aft surfaces of the wheel. One of the transducers serves to generate an ultrasonic signal, while ultrasonic signals reflected from acoustical discontinuities being received by the second transducer. The second common technique is referred to as pulse-echo and makes use of a single transducer to both generate the ultrasonic signal and receive reflected signals.

Inspections targeting axial-radial defects are performed routinely on steam turbine discs with shrunk-on wheels. Stress corrosion cracking typically develops at the surface of the central bore, and such cracks can be located using the pitch-catch technique in which the ultrasonic signals are targeted at the bore and the keyway surfaces at the perimeter of the wheel. This technique is not intended for full volumetric inspection of the wheel. A nondestructive testing method using the pitch-catch technique is also disclosed in U.S. Pat. No. 5,189,915 to Reinhart et al., whereby wheel blade attachment locations can be inspected ultrasonically from the bore of the wheel. Another pitch-catch technique has been developed for gas turbine wheels in the as-forged condition, at which time the wheels have parallel sides so that the technique is relatively simple to execute.

A pitch-catch inspection technique using transducers placed on the fore and aft faces of a gas turbine wheel following final machining would also seem the most likely technique to detect flaws having an axial-radial orientation throughout the wheel volume. However, axial-radial defects are difficult to detect in gas turbine wheels due to their complex geometry resulting from the final machining operation, which includes the machining of circumferentially-spaced bolt holes spaced radially from the central bore. A pitch-catch inspection of such a wheel would require a complex movement of the transducers and control of transducer angles to ensure an effective examination. Such an approach would be further exacerbated by the high sonic noise produced by the large material grain size as well as a tendency for the acoustic pulse to be steered by flow lines produced during the forging process.

In view of the above, it would be desirable if an improved method were available for ultrasonically inspecting articles having complex geometries, such as gas turbine wheels following final machining.

SUMMARY OF INVENTION

The present invention provides a method and system for ultrasonically inspecting turbine wheels and other disk-shaped articles having a central opening and a plurality of secondary openings radially spaced outward from the central opening. The method and system make use of at least one ultrasonic transducer placed in at least one of the secondary openings of the article. The ultrasonic transducer is configured and oriented to perform a pulse-echo diagnostic technique on the article by emitting ultrasonic signals that intersect radials of the article at angles of approximately ninety degrees to the radials, with the result that the ultrasonic signals intersect the radials at points so that a plurality of the points are located on a plurality of the radials. The points define a locus of points through the volume of the article between the central opening and the secondary opening, such that the volume is inspected for defects.

In view of the configuration and operation of the ultrasonic transducer, the method of this invention includes placing at least one ultrasonic transducer in at least a first of the secondary openings of the article, after which the transducer is caused to emit ultrasonic signals that intersect radials of the article at angles of approximately ninety degrees to the radials, such that a plurality of intersection points are located on a plurality of radials. The transducer is then used to receive reflected ultrasonic signals that return (are reflected) from one or more of the points, e.g., as a result of the presence of a defect at the point.

In view of the above, it can be seen that the present invention provides an inspection process that, when applied to a turbine wheel after final machining, makes use of holes spaced radially outward from the central hub bore. Such holes are commonly present as bolt holes machined near the rim area of a turbine wheel. When the pulse-echo ultrasonic technique is conducted from each bolt hole location, the existence of any axial-radial flaws within the wheel volume between the bolt hole and the central hub bore can be determined along the locus of points inspected with the ultrasonic signals, which includes the critical volume of the wheel immediately adjacent the central hub bore. As such, the present invention provides a method for ultrasonically inspecting turbine wheels and other articles having complex machined geometries.

The ultrasonic transducer is preferably one of multiple ultrasonic transducers assembled together as a unit that includes a specially shaped base whose shape conforms to the diameter of the hole in which the unit is placed. The method of this invention also preferably encompasses a technique by which the proper orientation of the transducers can be determined within the hole, and a method of calibrating the amplitude of reflected sound from a defect to an equivalent reference reflector.

Other objects and advantages of this invention will be better appreciated from the following detailed description.

DETAILED DESCRIPTION

Figure 1:
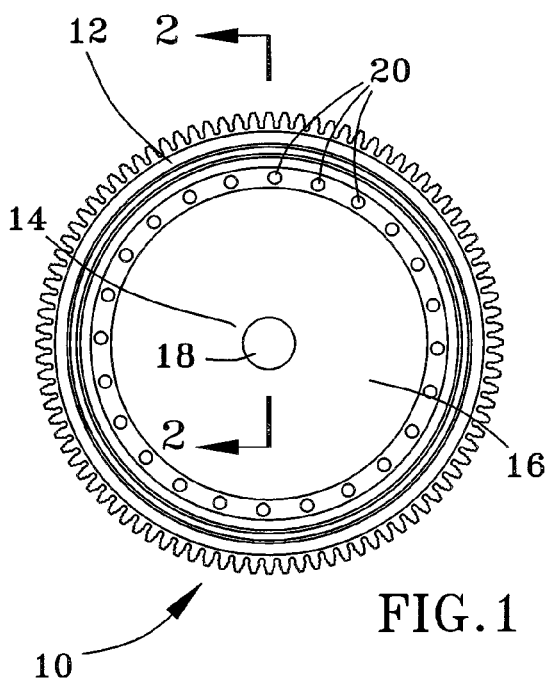
FIG. 1 shows a face of a gas turbine wheel in which an ultrasonic transducer unit is installed for performing a nondestructive ultrasonic inspection of the wheel in accordance with this invention.
Figure 2:
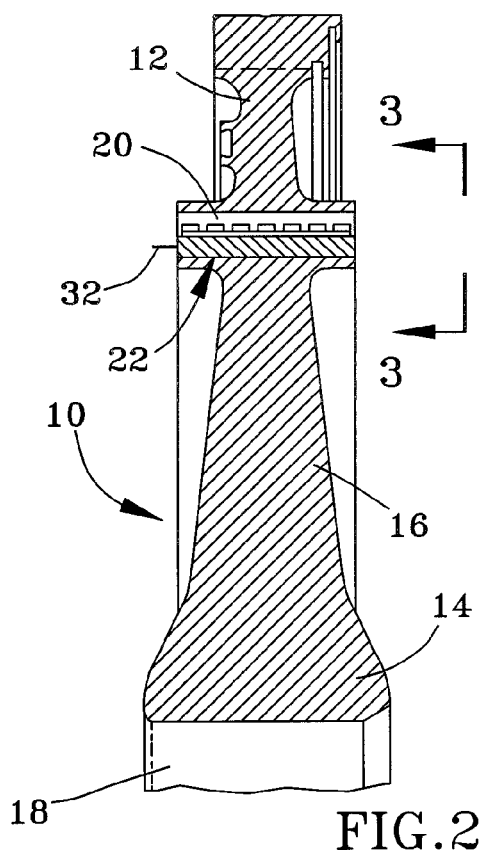
FIG. 2 is a partial cross-sectional view of the wheel of FIG. 1 along lines 2—2.

A gas turbine wheel 10 of a type known in the art is illustrated in FIGS. 1 and 2. The wheel 10 is represented as being in the final-machined condition, and generally includes a rim 12, a hub 14, and a web 16 between the rim and hub 12 and 14. The rim 12 is configured for the attachment of turbine blades (not shown) in accordance with known practice. A hub bore 18 in the form of a through-hole is centrally located in the hub 14 for mounting the wheel 10 on a turbine axis, and therefore the axis of the hub bore 18 coincides with the axis of rotation of the wheel 10. A plurality of bolt holes 20 are machined through the web 16 at locations that are equal radial distances from the hub bore 18 (center-to-center), as well as circumferentially equally spaced from each other (center-to-center). The axes of the bolt holes 20 are shown as parallel to the axis of the hub bore 18.

Figure 3:
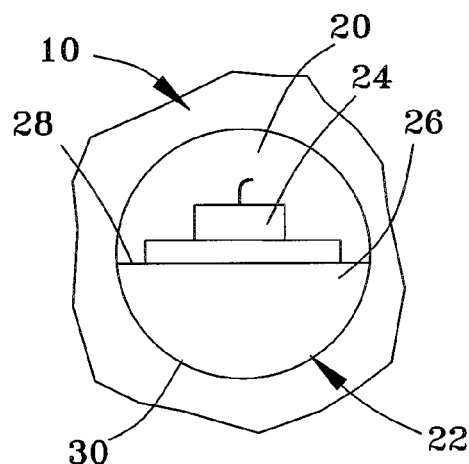
FIG. 3 is a view in the direction of line 3—3 of FIG. 2, showing in greater detail a transducer unit placed in a bolt hole of the wheel in accordance with a first embodiment of the invention.

From FIGS. 1 and 2, the complexity of the geometry of the wheel 10 is evident, making any ultrasonic inspection of the wheel 10 using conventional methods very difficult. According to the present invention, ultrasonic inspection of the wheel 10 is performed from the bolt holes 20 near the perimeter of the wheel 10, instead of the fore and aft faces of the wheel 10 or from the hub bore 18, as has been suggested in the past. For this purpose, a transducer unit 22 is shown in FIGS. 2 and 3 as being configured to fit within the bolt holes 20 and closely contact the curved surfaces of the bolt holes 20. As depicted in FIGS. 2 and 3, the unit 22 comprises several rectangular ultrasonic transducers 24 aligned in a row and mounted on a semi-cylindrical wedge 26. The wedge 26 provides a flat surface 28 for mounting the transducers 24, and a curved surface 30 whose radius of curvature is closely matched to that of the bolt holes 20. By forming the wedge 26 of the same (or similar) material as the wheel 10, the sound velocity in the wedge 10 is the same or nearly the same as in the wheel 10, so that the effect of the curvature of the bolt hole 20 is minimal. A suitable couplant, such as light weight turbine oil, can be applied between the curved surface 30 of the wedge 26 and the mating surface of the bolt hole 20 to further reduce the effect of the interface between the transducers 24 and the bolt hole 20. The wedge 26 is shown in FIG. 2 as being equipped with a handle 32 to facilitate placement and removal of the unit 22 from the bolt holes 20.

The transducers 24 can be of any type suitable for use in ultrasonic inspection procedures, such as a style RHP gamma series (or equivalent) available from Krautkramer, Inc. The width of the transducers 24 are preferably maximized to fit into the bolt holes 20, with minimal separation between elements. The height of each transducer 24 is preferably equal to or greater than its width in order to promote the signal-to-noise response from a defect reflector. In the configuration shown in FIGS. 2 and 3, the transducers 24 are arranged on the transducer unit 22 as a linear array, and as such can share a single pulser. The transducers 24 produce a longitudinal wave at a fixed angle of zero degrees normal to the surface of the wedge 26 on which the transducers 24 are mounted. Groups of the transducers 24 can be pulsed simultaneously or multiplexed to simulate movement in the axial direction. The entire group of transducers 24 can be rotated to provide radial coverage along a loci 40 of points 36 (FIG. 5).

Figure 5:
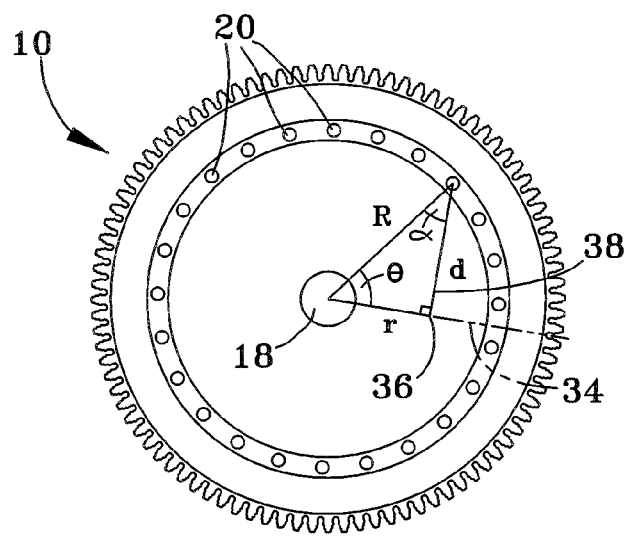
FIGS. 5, 6 and 7 graphically illustrates the ultrasonic inspection technique of the invention.
Figure 6:
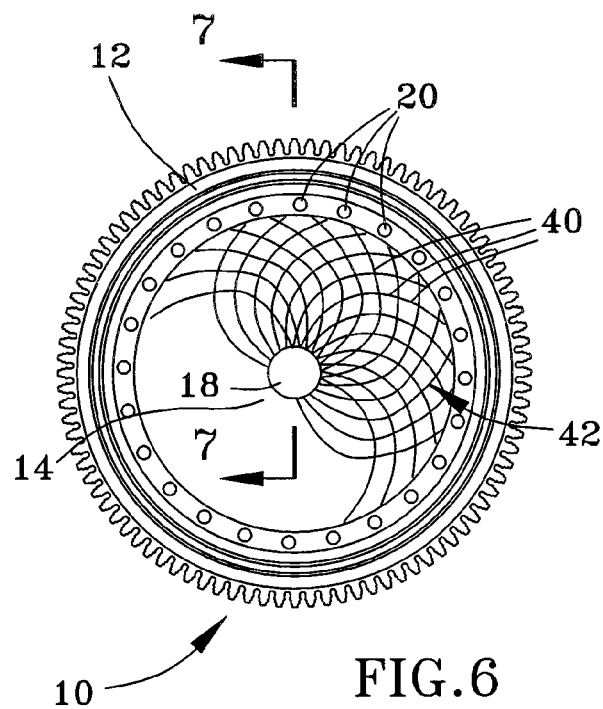

According to one aspect of the invention, the position of the transducer unit 22 for proper orientation of the transducers 24 is determined so that the ultrasonic signals generated by the transducers 24 intersect axial-radial type defects throughout the volume of the wheel 10 between the bolt holes 20 and the hub bore 16, as shown in FIGS. 5 and 6. In FIG. 5, the center-to-center distance between each bolt hole 20 and the hub bore 18 is identified as a constant distance R along a radial of the wheel 10. FIG. 5 further represents an ultrasound signal transmitted from one of the bolt holes 20 along a path 38 that is perpendicular to a second radial 34 of the wheel 10, intersecting the radial 34 at a point 36 located a distance d from the center of the bolt hole 20 and located a distance r from the center of the hub bore 18. The distances R, d and r define sides of a right triangle with an angle of ninety degrees between the sides corresponding to the radial 34 and signal path 38 (distances r and d, respectively), an angle α between the sides corresponding to the signal path 38 and the radial between the bolt hole 20 and the hub bore 18 (the distances d and R, respectively), and an angle θ between the sides corresponding to the radial 34 intersected by the signal and the radial between the bolt hole 20 and the hub bore 18 (the distances r and R, respectively). With this relationship, r=R sin α and d=R sin θ. The triangle depicted in FIG. 5 is just one of essentially an infinite number of triangles defined by ultrasonic signals intersecting an infinite number of radials 34 oriented at different angles θ from the radial through the hub bore 18 and the bolt hole 20 from which the signals are broadcast. The locus 40 of points 36 where the sound beam from the bolt hole 20 intersects these radials 34 of the wheel 10 at ninety degrees (perpendicular) is defined by the following equation:

$$\cos^2 \theta + \cos^2 \alpha = 1$$

The above equation defines the inspection coverage because at these positions the sound beam is perpendicular to a defect with orientation in the axial-radial plane. The transducer position within the bolt hole 20 is determined by physically rotating the transducer unit 22 within the hole 20. For example, the unit 22 is initially positioned in the hole 20 to maximize the reflection from the hub bore 18, and then rotated to follow the locus 40 of points 36 identified by the above equation. The maximized reflection from the bore 18 can be used to calibrate the inspection so indications can be sized relative to an equivalent flat bottom hole (FBH) reflector, as discussed below.

Figure 7:
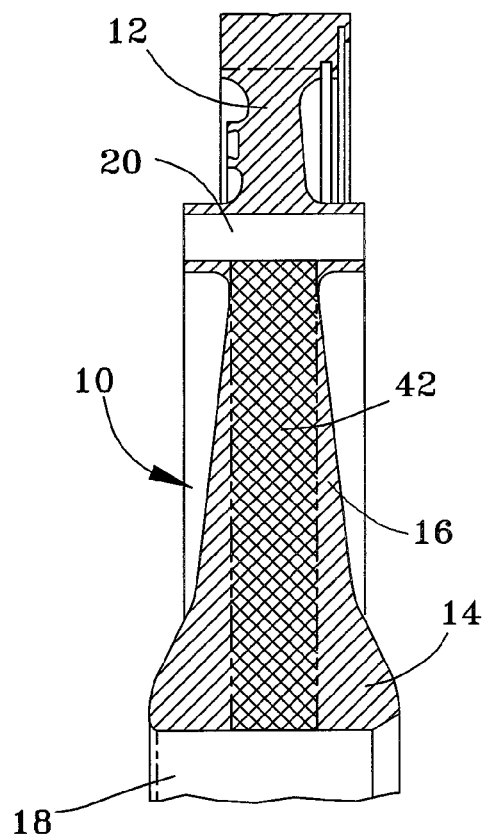

FIG. 6 plots multiple loci 40 of points 36 resulting from ultrasonic signals transmitted from over half of the bolt holes 20 of the wheel 10, and evidences that these loci 40 of points 36 provide coverage of a substantial annular-shaped volume 42 of the wheel 10 lying between the hub bore 18 and the circle along which the bolt holes 20 lie. The volume 42 is defined by only those loci 40 of points 36 established by perpendiculars between the bolt holes 20 and the wheel radials 34. With sound beam spread that inherently occurs, the volume 42 of the wheel 10 covered by the loci 40 can be increased slightly depending on the particular transducer parameters used. In any event, the volume 42 of material that can be inspected positively coincides with the region within the wheel 10 in which critical defects typically occur, as represented in FIGS. 6 and 7.

According to another aspect of this invention, a method is provided for calibrating the amplitude of reflected sound to standard calibration reflectors, known as flat bottom holes (FBH). The method involves establishing a predetermined amplitude response from an ultrasonic signal reflected from the wall of the hub bore 18, which permits a relationship between the indication amplitude and the FBH size to be calculated using the following equation:

$$A_f = \lambda d^2 P_f (b/R)^{1/2}/(2(R-b)P_R)$$

where $A_f$ is the area of the FBH, $\lambda$ is the wavelength of sound in the turbine wheel 10, d is the sound path distance between the transducer 24 and an indication (defect), $P_f$ is the amplitude of the reflected ultrasonic signal from the indication, b is the radius of the hub bore 18, R is the distance between the centers of the hub bore 18 and the bolt holes 20, and $P_R$ is the amplitude of the reflected calibration ultrasonic signal from the hub bore 18. This equation is derived as follows. The sound pressure along the axis of one of the transducers 24 is:

$$P = p_0 2 \sin(\Pi((D/2)^2 + d^2)^{1/2} - d)/\lambda)$$

where P is the on-axis pressure in the direction of sound travel, $p_0$ is the original pressure at the material surface, and D is the diameter of the transducer's disc-shaped oscillator (J. Krautkramer et al., Ultrasonic Testing of Materials, 4$^{th}$ edition, Springer-Verlag (1990), p. 70). For large values of d and D/$\lambda$, and for non-circular transducers, this may be simplified as $$P = p_0 A/\lambda d$$

where A is the area of the oscillator (J. Krautkramer et al. at p. 71). Using this relationship, the sound pressure measured from the large bore reflection can be expressed as:

$$P_R = p_0 A_T (b/R)^{1/2}/2\lambda(R-b)$$

and the sound pressure measured from a flaw is given by:

$$P_f = p_0 (A_T/\lambda d) \times (A_f/\lambda d)$$

where $A_T$ is the area of the oscillator and $A_f$ is the area of the flaw. Solving the last two equations for $A_f$ yields the above-identified expression for determining the area of an equivalent flat bottom hole (FBH), namely, $$A_f = \lambda d^2 P_f (b/R)^{1/2}/(2(R-b)P_R)$$

Figure 4:
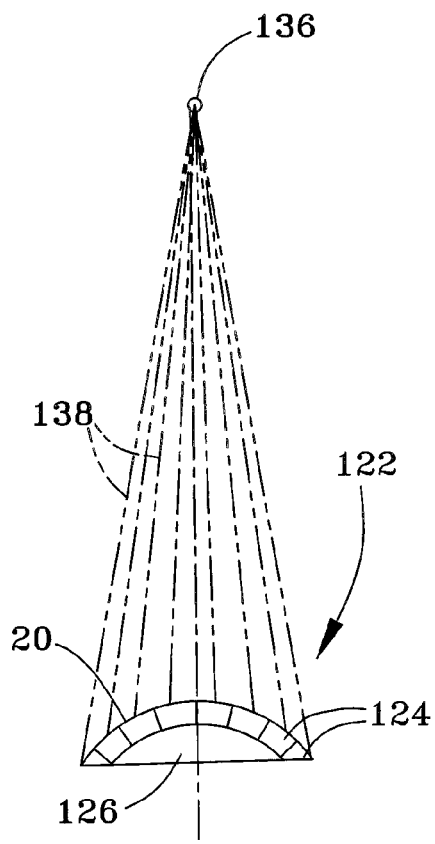
FIG. 4 schematically represents a transducer unit in accordance with a second embodiment of the invention.

In an alternative embodiment of the invention, the linear array transducer unit 22 represented in FIGS. 2 and 3 is replaced with a phased array transducer unit 122 represented in FIG. 4. As the term phased array is conventionally understood in the art, the transducer unit 122 comprises a series of individual ultrasonic transducers 124 arranged in a row and acoustically isolated from each other. Contrary to the linear array unit 22 of FIGS. 2 and 3, each transducer 124 has its own electrical connection and pulser (not shown), and each produces its own radio-frequency time/amplitude response (A-scan), which can then be summed and graphically displayed. The angle of the ultrasonic beam 138 generated by each transducer 124 is varied (steered) as well as the mode and focus of the beam 138 by controlling the timing of the pulse and reception for each individual transducer 124. The advantage of using the phased array transducer 122 in the inspection method of this invention is the ability to focus the ultrasonic signal at a specific target 136 at a specific depth. This focusing of the sound beam 138 counteracts the negative effect that the curvature of the bolt holes 20 has on the sound field, which would disperse the sound beam 138 and reduce the sound amplitude reflected from a defect.

The phased array transducer unit 122 represented in FIG. 4 comprises eight transducers 124. The actual number of elements (N) used with the method of this invention will vary depending on the spacing between elements (k), the wavelength ($\lambda$) of sound in the metal, the sound beam divergence angle ($\alpha$) to the target 136, and the active length (L) of the transducer unit 122. This relationship is given by the following equation:

$$N = (L+k) \sin \alpha/(0.44\lambda + k \sin \alpha)$$

The optimum length (L) of the unit 122 can be determined by solving the following equation for L using the maximum distance (d) from the center of the bolt hole 20 to the target 136 and the radius (r) of the bolt hole 20:

$$d^2 + r^2 - 2dr \cos(L/2r) - d^2 \sin^2(L/2r)/\sin^2 \alpha = 0$$

The calibration of the phased array transducer unit 122 of FIG. 4 can be accomplished using a Distance-Gain-Size (DGS) technique that relates the amplitude of reflected sound from the hub bore 18 of the turbine wheel 10 to the amplitude response from known size flat bottom holes (FBH) at varying distances from the unit 122. A DGS diagram can be obtained through computer modeling of the sound field responses or can be determined empirically using geometrically equivalent calibration blocks containing machined FBH reflectors.

While the invention has been described in terms of particular embodiments, it is apparent that other forms could be adopted by one skilled in the art. For example, the physical configurations of the units 22 and 122 and of the article (e.g., wheel 10) being inspected with the units 22 and 122 could differ from that shown. Therefore, the scope of the invention is to be limited only by the following claims.

What is claimed is:

1. A method of ultrasonically inspecting a disk-shaped article having a central opening and a plurality of secondary openings radially spaced outward from the central opening and circumferentially spaced from each other, the method comprising the steps of:
   placing at least one ultrasonic transducer in at least a first of the secondary openings of the article;
   performing a pulse-echo diagnostic technique on the article by causing the transducer to emit ultrasonic signals that intersect radials of the article at angles of approximately ninety degrees to the radials, the ultrasonic signals intersecting the radials at points so that a plurality of the points are located on a plurality of the radials;
   receiving with the transducer a reflected ultrasonic signal that is returned from at least one of the plurality of points;
   calibrating the amplitude of the reflected ultrasonic signal to a flat bottom hole standard reflector by causing the transducer to emit a calibration ultrasonic signal toward the central opening and receiving a reflected calibration ultrasonic signal from the central opening, and calculating a relationship between the amplitude of the reflected ultrasonic signal returned from the one point to the flat bottom hole standard reflector according to the equation:

$$A_f = \lambda d^2 P_f (b/R)^{1/2}/(2(R-b)P_r)$$

where $A_f$ is the area of the flat bottom hole standard reflector, $\lambda$ is the wavelength of sound in the article, d is the distance between the transducer and the at least one of the points, $P_f$ is the amplitude of the reflected ultrasonic signal from the at least one of the points, b is the radius of the central opening, R is the distance between a center of the first secondary opening and a center of the central opening along one of the radials of the article, and $P_r$ is the amplitude of the reflected calibration ultrasonic signal from the central opening.

2. The method according to claim 1, wherein the at least one ultrasonic transducer is one of an array of ultrasonic transducers placed in the first secondary opening, the ultrasonic transducers being pulsed simultaneously during the performing step.

3. The method according to claim 1, wherein the at least one ultrasonic transducer is one of an array of ultrasonic transducers placed in the first secondary opening, at least some of the ultrasonic transducers being pulsed at different times during the performing step.

4. The method according to claim 1, wherein the at least one ultrasonic transducer is one of a phased array of ultrasonic transducers placed in the first secondary opening, the phased array of ultrasonic transducers being operated to focus the ultrasonic signals at predetermined depths from the first secondary opening.

5. The method according to claim 1, wherein the central opening is a through-hole having an axis of symmetry and each of the secondary openings is a through-hole having an axis of symmetry that is substantially parallel to the axis of the central opening.

6. The method according to claim 1, wherein all of the plurality of points are located between the central opening and a circle concentric with the central opening and on which the first secondary opening is located.

7. The method according to claim 1, wherein the at least one ultrasonic transducer is one of an array of ultrasonic transducers mounted on a body to form a transducer unit, the placing step comprising placing the transducer unit in the first secondary opening, the body having a semicircular cross-section with a radius of curvature approximately equal to a radius of curvature of the first secondary opening.

8. The method according to claim 7, wherein the article and the body on which the transducer unit is mounted are formed of the same material.

9. The method according to claim 1, wherein the first secondary opening has a center located a constant distance R from a center of the central opening along one of the radials of the article, and each of the points is located a distance d from the center of the secondary opening and a distance r from the center of the central opening, the distances R, d and r defining sides of a right triangle with an angle of ninety degrees between the sides corresponding to the distances d and r, an angle $\alpha$ between the sides corresponding to the distances d and R, an angle $\theta$ between the sides corresponding to the distances r and R, wherein the plurality of points are located by the equation:

$$\cos^2 \theta + \cos^2 \alpha = 1.$$

10. The method according to claim 1, wherein all of the points are located within an intermediate portion of the article between the central opening and the first secondary opening.

11. The method according to claim 1, wherein the article is a machined gas turbine wheel, the central opening is an inner hub bore of the wheel, and the secondary openings are bolt holes of the wheel.

12. A method of ultrasonically inspecting a turbine wheel having a central hub bore, a plurality of bolt holes radially spaced outward from the central hub bore and circumferentially spaced from each other along a circle concentric with the central hub, and an annular-shaped web region between the central hub bore and the bolt holes, the wheel being formed such that the web region potentially contains axial-radial oriented defects, the method comprising the steps of:

mounting a plurality of ultrasonic transducers to form at least one transducer unit;

placing the transducer unit in a first of the bolt holes of the turbine wheel;

performing a pulse-echo diagnostic technique on the turbine wheel by causing the ultrasonic transducers to emit ultrasonic signals that intersect radials of the turbine wheel at angles of approximately ninety degrees to the radials, the ultrasonic signals intersecting the radials at points located within the web portion of the wheel between the central hub bore and the first bolt hole so that each of a plurality of the points is located on a corresponding one of the radials, all of the plurality of points being located within the web portion; and placing the transducer unit in a sufficient additional number of the bolt holes and performing the pulse-echo diagnostic technique on the wheel to locate additional points throughout the web portion;

wherein at least one of the ultrasonic transducers receives at least one reflected ultrasonic signal returned from at least one of the plurality of points at which an axial-radial oriented defect is present and oriented substantially perpendicular to the ultrasonic signal that returned the reflected ultrasonic signal; and wherein each of the bolt holes has a center located a constant distance R from a center of the central hub bore along one of the radials of the turbine wheel, each of the plurality of points is located a distance d from the center of the bolt hole and a distance r from the center of the central hub bore, the distances R, d and r define sides of a right triangle with an angle of ninety degrees between the sides corresponding to the distances d and r, an angle $\alpha$ between the sides corresponding to the distances d and R, and an angle $\theta$ between the sides corresponding to the distances r and R, and the plurality of points are located within the turbine wheel by the equation:

$$\cos^2 \theta + \cos^2 \alpha = 1.$$

13. The method according to claim 12, wherein the ultrasonic transducers are pulsed simultaneously during the performing steps.

14. The method according to claim 12, wherein the ultrasonic transducers are pulsed at different times during the performing steps.

15. The method according to claim 12, wherein the plurality of ultrasonic transducers is a phased array and the ultrasonic transducers are operated to focus the ultrasonic signals at predetermined depths from the bolt holes.

16. The method according to claim 12, wherein the transducer unit comprises the plurality of ultrasonic transducers and a body on which the plurality of ultrasonic transducers are mounted, the body having a semicircular cross-section with a radius of curvature approximately equal to a radius of curvature of the bolt holes.

17. The method according to claim 16, wherein the turbine wheel and the body on which the plurality of ultrasonic transducers are mounted are formed of the same material.

18. The method according to claim 12, wherein the step of performing the pulse-echo diagnostic technique on the turbine wheel is repeated for each of the bolt holes using the at least one transducer unit or another of the at least one transducer.

19. The method according to claim 12, further comprising the step of calibrating the amplitude of the reflected ultrasonic signals returned from the plurality of points to a flat bottom hole standard reflector by causing the transducer to emit a calibration ultrasonic signal toward the central hub bore and obtaining a reflected calibration ultrasonic signal from the central hub bore, and then calculating a relationship between the amplitude of the reflected ultrasonic signals returned from the plurality of points to the flat bottom hole standard reflector according to the equation:

$$A_f = \lambda d^2 P_f (b/R)^{1/2} / (2(R-b) P_r)$$

where $A_f$ is the area of the flat bottom hole standard reflector, $\lambda$ is the wavelength of sound in the wheel, d is the distance between the transducer and the at least one of the points, $P_f$ is the amplitude of the reflected ultrasonic signal from the at least one of the points, b is the radius of the central hub bore, R is the distance between a center of the first bolt hole and a center of the central hub bore along one of the radials of the wheel, and $P_r$ is the amplitude of the reflected calibration ultrasonic signal from the central hub bore.

* * * * *